United States Patent
Wahrenberg

(10) Patent No.: US 12,243,249 B2
(45) Date of Patent: Mar. 4, 2025

(54) VOLUME RENDERING APPARATUS AND METHOD

(71) Applicant: CANON MEDICAL SYSTEMS CORPORATION, Otawara (JP)

(72) Inventor: Magnus Fredrik Wahrenberg, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 376 days.

(21) Appl. No.: 17/660,065

(22) Filed: Apr. 21, 2022

(65) Prior Publication Data

US 2023/0342957 A1     Oct. 26, 2023

(51) Int. Cl.
| | |
|---|---|
| *G06T 7/00* | (2017.01) |
| *G06T 5/50* | (2006.01) |
| *G06T 7/11* | (2017.01) |
| *G06T 7/38* | (2017.01) |
| *G06V 10/25* | (2022.01) |

(52) U.S. Cl.
CPC .............. *G06T 7/38* (2017.01); *G06T 5/50* (2013.01); *G06T 7/0012* (2013.01); *G06T 7/11* (2017.01); *G06V 10/25* (2022.01)

(58) Field of Classification Search
CPC ........... G06T 5/50; G06T 7/00; G06T 7/0012; G06T 7/11; G06T 7/38; G06V 10/25
See application file for complete search history.

(56) References Cited

U.S. PATENT DOCUMENTS

| | | | |
|---|---|---|---|
| 8,605,185 B2 * | 12/2013 | Border | H04N 9/8205 |
| | | | 348/222.1 |
| 9,717,415 B2 * | 8/2017 | Cohen | G06T 7/0014 |
| 2007/0092110 A1 | 4/2007 | Xu et al. | |
| 2012/0134553 A1 | 5/2012 | Liao et al. | |
| 2018/0042698 A1 | 2/2018 | Salah et al. | |
| 2018/0268237 A1 | 9/2018 | Stanimirovic et al. | |
| 2019/0159737 A1 | 5/2019 | Buckler et al. | |
| 2020/0099862 A1 * | 3/2020 | Yao | H04N 23/683 |
| 2022/0211449 A1 * | 7/2022 | Rentschler | G06T 7/66 |

FOREIGN PATENT DOCUMENTS

| | | |
|---|---|---|
| EP | 1 683 108 A2 | 7/2006 |
| JP | 2020-049204 A | 4/2020 |
| WO | WO 2005/048196 A2 | 5/2005 |

* cited by examiner

*Primary Examiner* — Tuan H Nguyen
(74) *Attorney, Agent, or Firm* — Oblon, McClelland, Maier & Neustadt, L.L.P.

(57) ABSTRACT

A medical image display apparatus comprises processing circuitry configured to: receive a plurality of frames each comprising respective medical image data; specify an order of priority for the plurality of frames; select regions of medical image data from more than one of the frames of the plurality of frames based on the order of priority; and generate combined image data by combining the selected regions of medical image data, such that different regions of the combined image data comprise medical image data from different ones of the plurality of frames.

17 Claims, 10 Drawing Sheets

VOLUME RENDERING APPARATUS AND METHOD

FIELD

Embodiments described herein relate generally to an apparatus and method for volume rendering, for example to create a combined image using medical image data from a plurality of frames.

BACKGROUND

Volumetric medical imaging techniques that can produce three-dimensional (3D) medical image data using any of a variety of imaging modalities, for example CT, PET, MRI, ultrasound, and X-ray, are now widely used for imaging or diagnostic purposes.

It is also known to acquire four-dimensional (4D) medical imaging data that is representative of motion. The 4D medical imaging data is representative of three spatial dimensions plus time. A 4D acquisition may be displayed as an animated sequence of a 3D view.

A data set that is representative of motion over time may be referred to as a temporal data set. More and more temporal data sets are being used in modern medical imaging.

Typically, 3D data is more complex to view than 2D data. Similarly, 4D data is even more complicated than 3D to show and integrate.

An action sequence is the process of combining a sequence of animation into one image. An action sequence is an established concept in photography. An action sequence may be obtained by compositing multiple images into the same scene.

FIG. 1 shows an example of an action sequence. Movement of a volleyball player is represented by compositing multiple images of the volleyball player that have been obtained at successive times. This results in multiple instances 12A to 12I of the volleyball player in a single composite action sequence image 10. Over time, the volleyball player moves from the left of FIG. 1 to the right of FIG. 1. The action sequence provides a way of representing movement within a static image.

Generating an action sequence such as that shown in FIG. 1 depends on spatial separation and separation of foreground and background. Each instance 10A to 10I of the volleyball player is separated in space. In each of a set of individual images to be composited, the background is extracted from the foreground. The foreground comprises the volleyball player and ball. In the compositing of the images to form the action sequence image 10, multiple foregrounds are added to a common background.

In medical images, there is interest in creating views that combine complex volume data into a single image. Examples include curved planar reformatting, dissected colon, and ribcage reformats. 3D images may be reformatted into 2D images. Instead of navigating multiple images, a user may instead be presented with a single summary view.

Some forms of medical imaging may produce animated sequences, for example ultrasound and angiography. It may be desirable to produce a summary visualization of an animated sequence. However, in a medical context, it is rare to have a sequence of images that have a natural spatial separation.

BRIEF DESCRIPTION OF THE DRAWINGS

Embodiments are now described, by way of non-limiting example, and are illustrated in the following figures, in which.

DETAILED DESCRIPTION

Certain embodiments provide a medical image display apparatus comprising processing circuitry configured to: receive a plurality of frames each comprising respective medical image data; specify an order of priority for the plurality of frames; select regions of medical image data from more than one of the frames of the plurality of frames based on the order of priority; and generate combined image data by combining the selected regions of medical image data, such that different regions of the combined image data comprise medical image data from different ones of the plurality of frames.

Certain embodiments provide a method comprising: receiving a plurality of frames each comprising respective medical image data; specifying an order of priority for the plurality of frames; selecting regions of medical image data from more than one of the frames of the plurality of frames based on the order of priority; and generating combined image data by combining the selected regions of medical image data, such that different regions of the combined image data comprise medical image data from different ones of the plurality of frames.

Figure 2:
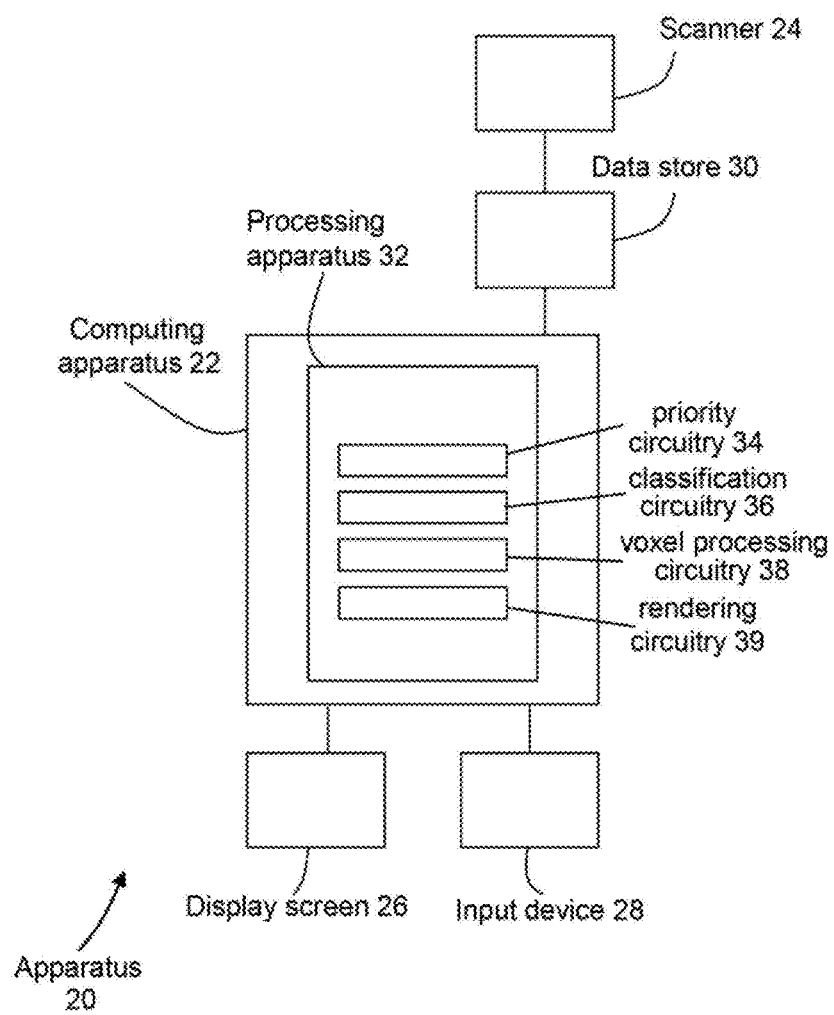
FIG. 2 is a schematic diagram of an apparatus according to an embodiment.

A medical image processing apparatus 20 according to an embodiment is illustrated schematically in FIG. 2. The medical image processing apparatus 20 may also be referred to as a medical image display apparatus. The medical image processing apparatus 20 comprises a computing apparatus 22, in this case a personal computer (PC) or workstation, which is connected to a scanner 24 via a data store 30.

The medical image processing apparatus 20 further comprises one or more display screens 26 and an input device or devices 28, such as a computer keyboard, mouse or trackball.

In the present embodiment, the scanner 24 is an ultrasound scanner configured to obtain volumetric ultrasound data using an ultrasound probe (not shown in FIG. 2).

The scanner 24 is configured to generate image data that is representative of volume comprising at least one anatomical region of a patient or other subject. The image data represents a plurality of voxels each having a corresponding image data value.

In further embodiments, the scanner 24 may be configured to obtain two-, three- or four-dimensional image data in any imaging modality. For example, the scanner 34 may comprise a magnetic resonance (MR) scanner, computed tomography (CT) scanner, cone-beam CT scanner, positron emission tomography (PET) scanner, X-ray scanner, or ultrasound scanner.

In the present embodiment, image data sets obtained by the scanner 24 are stored in data store 20 and subsequently provided to computing apparatus 22. In an alternative embodiment, image data sets are supplied from a remote data store (not shown). The data store 30 or remote data store may comprise any suitable form of memory storage.

In some embodiments, the medical image processing apparatus 20 is not coupled to any scanner.

Computing apparatus 22 comprises a processing apparatus 32 for processing of data. The processing apparatus comprises a central processing unit (CPU) and Graphical Processing Unit (GPU). The processing apparatus 32 provides a processing resource for automatically or semi-automatically processing medical image data sets. In other embodiments, the data to be processed may comprise any image data, which may not be medical image data.

The processing apparatus 32 includes priority circuitry 34 which is configured to determine an order of priority for a plurality of frames, classification circuitry 36 which is configured to classify regions of voxels, voxel processing circuitry 38 which is configured to process voxels and save voxel information; and rendering circuitry 39 which is configured to perform image rendering.

In the present embodiment, the circuitries 34, 36, 38, 39 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

Figure 3:
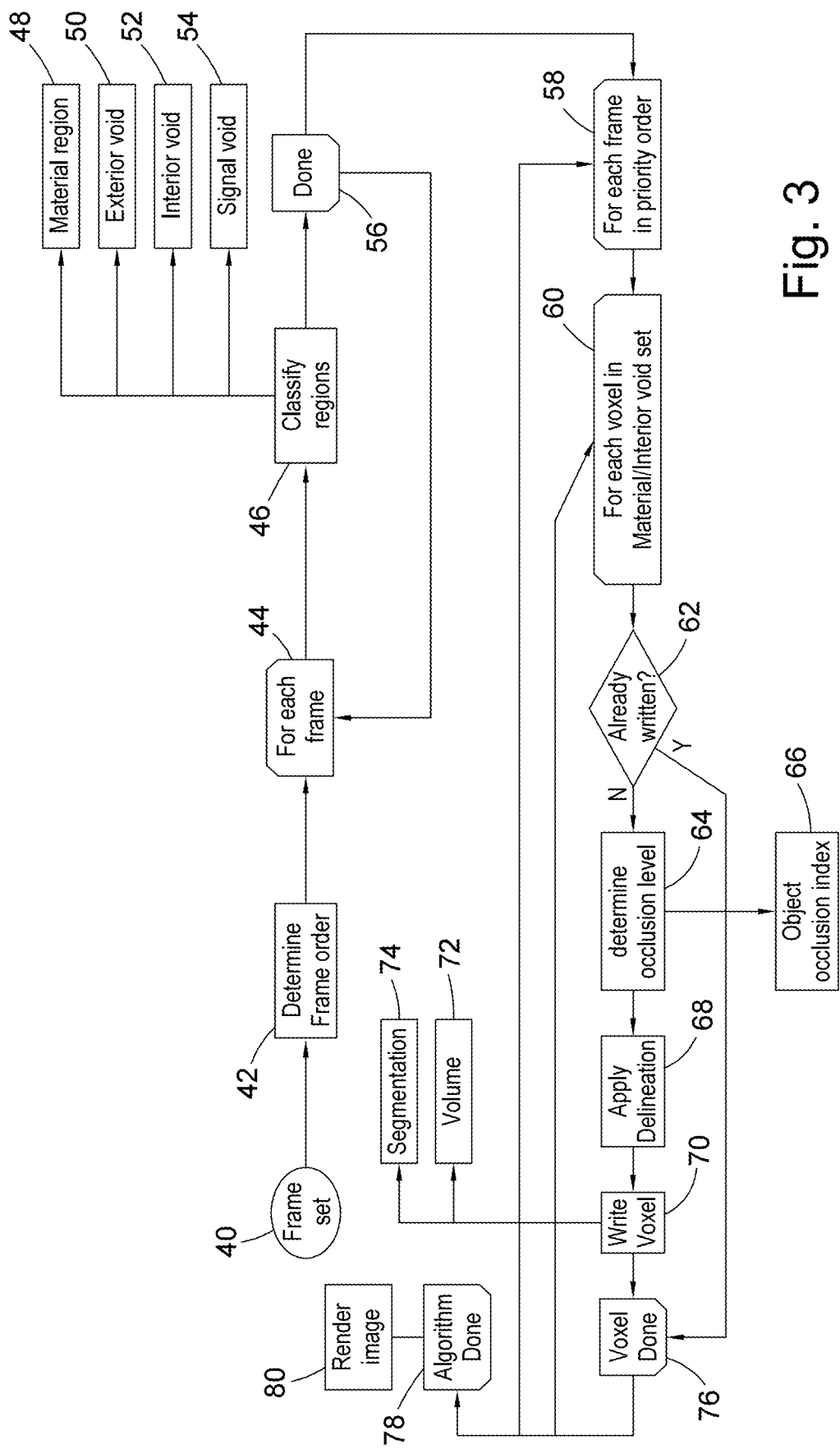
FIG. 3 is a flow chart illustrating in overview a method in accordance with an embodiment.

FIG. 3 is a flow chart illustrating in overview a method of an embodiment, which may be performed using the apparatus of FIG. 2. In the method of FIG. 3, an image is rendered using information from a plurality of frames. The frames are combined using a plurality order to provide an action sequence image.

Figure 1:
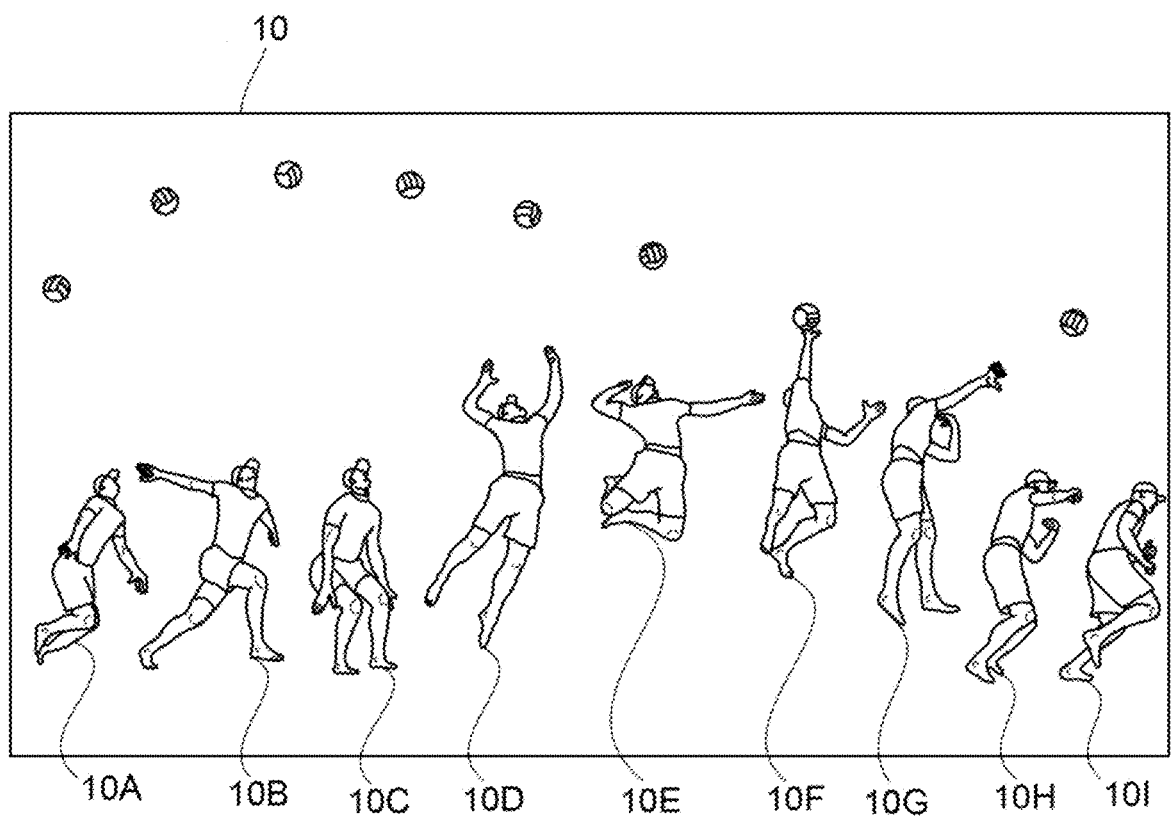
FIG. 1 is an example of an action sequence.

In medical images, sequences of frames may not have a natural spatial separation such as that shown in FIG. 1, in which an object occupies different and non-overlapping positions in successive frames. Therefore, in the method of FIG. 3, contributions of frames are divided into segmentation objects. Material that occludes material from a higher-priority frame is treated differently from non-occluding material.

Figure 4A:
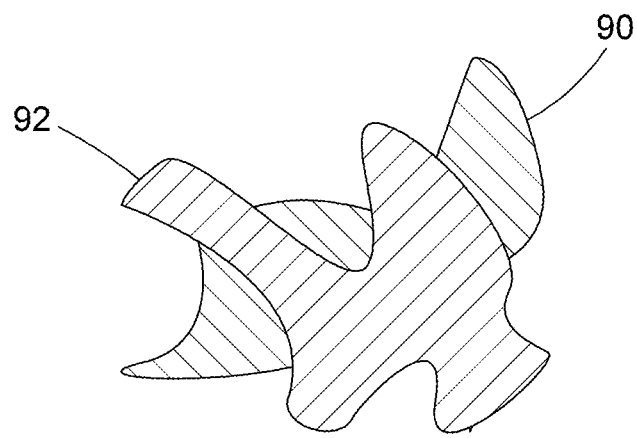
FIG. 4A illustrates an example of a rendering in which a high priority object is occluded by a low priority object.
Figure 4B:
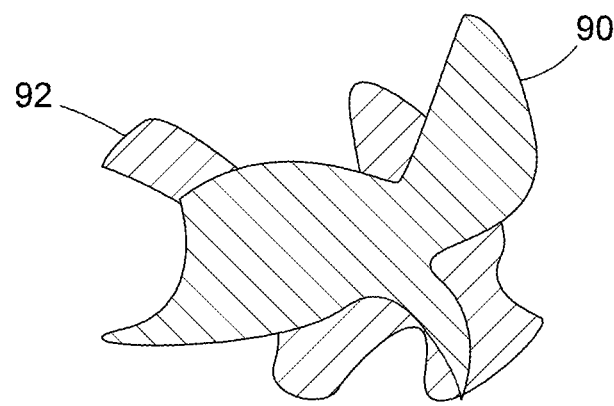
FIG. 4B illustrates an example of a rendering in which a low priority object is occluded by a high priority object.
Figure 4C:
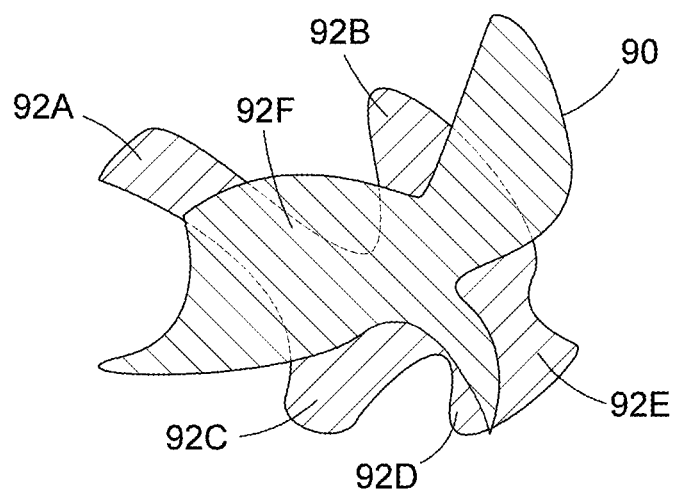
FIG. 4C schematically illustrates an example of a rendering in which a part of a low-priority object that occludes a high-priority object is rendered with lower opacity than a non-occluding part of the low priority object.

FIGS. 4A to 4C schematically illustrate different ways of rendering objects in different frames, taking into account occlusion. Object 90 is a region of material from a high priority frame. Object 90 may be described as a high priority object. Object 92 is a region of material from a low priority frame. Object 92 may be described as a low priority object. The aim of the rendering is to display information from both frames in a single image.

In FIG. 4A, the rendering is such that the high priority object 90 is occluded by the low priority object 92. The high priority object 90 is rendered as a solid object. The low priority object is rendered as a solid object occluding the high priority object 90. Such a rendering may be considered to be undesirable, since parts of the high priority object are hidden by something that is lower priority.

In FIG. 4B, the rendering is such that the low priority object 92 is occluded by the high priority object 90. Each of the high priority object 90 and low priority object 92 is rendered as a solid object. The rendering of FIG. 4B may be considered to be adequate.

In FIG. 4C, occluding material of the low priority object 92 is separated from material that is not occluding to split the low priority object 92 into several component objects 92A, 92B, 92C, 92D, 92E, 92F. Non-occluding or background material of component objects 92A, 92B, 92C, 92D, 92E is rendered as solid. This means that the parts of the low priority object 92 that do not occlude the high priority object 90 are rendered as solid. Component object 92F occludes the high priority object. Component object 92 may be faded or left as outline to avoid the occluding action. All of the high priority object 90 is visible in FIG. 4C. The rendering of FIG. 4C may provide a useful way of displaying both the high priority object 90 and the low priority object 92 in a single image. An occlusion issue may be considered to be corrected.

The method of FIG. 3 provides a method of rendering in which occluding material and non-occluding material are distinguished as described below.

Turning to FIG. 3, at stage 40 of FIG. 3 the priority circuitry 34 receives a frame set. The frame set comprises image data obtained in a succession of image acquisitions, for example as frames of a four-dimensional image acquisition. The image data may be obtained using any suitable scan modality, for example ultrasound or CT. The frames of the frame set are representative of a volume having an associated coordinate system. Each frame comprises a respective volumetric image data set comprising voxel values for voxels of the volume. The frames have an associated time order which is an order in which the frames were acquired, from a first frame that was acquired to a last frame that was acquired.

In other embodiments, the frame set may comprise frames that were acquired in different acquisitions, for example a scan and a follow-up scan. In some embodiments, an image registration process is used to register images from different frames of the frame set, for example if the frames were acquired in different acquisitions. The image registration may comprise rigid or non-rigid registration.

The voxel processing circuitry 38 receives or determines a viewing direction relative to the coordinate system of the plurality of frames. The viewing direction may be defined by the modality used to acquire the plurality of frames, for example if the modality is ultrasound or magnetic resonance. Alternatively, the viewing direction may be input by a user or may be determined in any suitable manner.

At stage 42, the priority circuitry 36 determines an order of priority for the frames. In the embodiment of FIG. 3, the order of priority of the frames is different from the time order of the frames. The priority circuitry 36 selects one of the frames as a top priority frame for display. The top priority frame may also be referred to as a current frame. The top priority frame may be any of the frames of the frame set. The top priority frame may be selected in response to a user input, for example in response to a selection by a user of one frame of the frame set. In other embodiments, the priority circuitry 36 may perform an automated selection of the top priority frame, for example by selecting a most significant frame of the plurality of frames.

The top priority frame is allocated a priority value of 1.

Other frames of the frame set are arranged in order of priority after the top priority frame. In the embodiment of FIG. 3, the frames are given increasing integer priority values. In other embodiments, any suitable system of priority values may be used. For example, the priority values may be any suitable number, letters or other indicators.

In the embodiment of FIG. 3, frames other than the top priority frame are ordered so that they alternate between future frames and past frames. Future frames are the frames that have an later acquisition time than the top priority frame. Past frames are the frames that have an earlier acquisition time than the top priority frame.

Consider an example in which five frames f1, f2, f3, f4, f5 are acquired at acquisition times t1, t2, t3, t4, t5 respectively, where t1 is the earliest time and t5 is the latest time.

Frame f3 is selected as the top priority frame so is first in the order of priority and is given a priority value of 1. The nearest future frame to the top priority frame, which is f4, is selected as the second frame in the order of priority and is given a priority value of 2. The nearest past frame to the top priority frame, which is f2, is selected as the third frame in the order of priority and is given a priority value of 3. The next future frame, which is f5, is selected as the fourth frame in the order of priority and is given a priority value of 4. The next past frame, which is f1, is selected as the fifth frame in the order of priority and is given a priority value of 5. The order of priority is therefore f3, f4, f2, f5, f1 and is different from the original time order of f1, f2, f3, f4, f5.

In the embodiment of FIG. 3, past and future frames are alternated to keep a consistent temporal distance. In other embodiments, a different order of priority may be used.

In some embodiments the order of priority favors future frames over past frames. A top priority frame is the first frame in the order of priority. The order of priority next includes the future frames, in time order. After the future frames, the order of priority turns to the past frames. The past frames may be included in reverse time order so that past frames that are closer in time to the top priority frame are higher in the order of priority than past frames that are further in time from the top priority frame. For example, in the case of time-ordered frames f1, f2, f3, f4, f5 in which f3 is the top priority frame, an order of priority that favors future frames over past frames may be f3, f4, f5, f2, f1.

In other embodiments, an order of priority favors past frames over future frames. For example, in the case of time-ordered frames f1, f2, f3, f4, f5 in which f3 is the top priority frame, an order of priority that favors future frames over past frames may be f3, f2, f1, f4, f5.

In some embodiments, an order of priority includes a top priority frame and one or more past frames without including future frames. In other embodiments, an order of priority includes a top priority frame and one or more future frames without including future frames. In some embodiments, an order of priority includes a top priority frame, all past frames, and a last future frame.

In further embodiments, any suitable order of priority may be used. Any of the frames may be selected as the top priority frame using any suitable selection method.

At stage 44, the classification circuitry 36 chooses a frame of the frame set for processing. For stages 44 to 56 of FIG. 3, the frames may be processed in any order. The classification circuitry 36 may choose any frame of the frame set, for example by choosing frames in priority order or in time order. In other embodiments, the frames may be processed in a fixed order, for example in order of priority or in time order.

At stage 46, the classification circuitry 36 classifies regions of the volumetric image data set for the chosen frame. In the embodiment of FIG. 3, voxels are classified as belonging to one of four classes. The first class is voxels belonging to a material region 48. The second class is voxels belonging to an exterior void 50. The third class is voxels belonging to an interior void 52. The fourth class is voxels belonging to a signal void 54.

An example of a material region 48 may be a region in which material is identified, for example a region in which tissue is identified. The material region 48 may comprise a single object, or may be the union of multiple objects. An example of an exterior void 50 may be, for example, an area around the body of a patient who has been scanned. An example of an interior void 52 may be, for example, a region of air within the body of the patient who has been scanned, for example a region of air in the colon. An example of a signal void 54 may be a region in which no data is available, or a region in which only weak data is available. For example, in ultrasound or magnetic resonance there may be areas in which no data or only weak data is available.

In other embodiments, any suitable classes may be used, and any suitable number of classes may be used. Different classes may be used from classes 48, 50, 52, 54 above. Certain ones of classes 48, 50, 52, 54 may be grouped together. One or more of classes 48, 50, 52, 54 may be divided into multiple classes.

In the embodiment of FIG. 3, the classifying is performed by thresholding image values of the voxels of the volumetric image data set, and then applying one or more morphological operators to segment regions of the different classes. For example, a threshold value may be used to distinguish material from void, and the one or more morphological operators may be used to distinguish exterior void from interior void. Finding the hull of the material region may be used to separate the interior void. In other embodiments, the classifying may comprise any suitable classification process, for example any suitable segmentation process.

At stage 56, the classification of regions of the chosen frame is finished. If more frames of the frame set remain to be classified, the process of FIG. 3 returns to stage 44 and the classification circuitry 36 chooses another frame for processing. If all the frames of the frame set have been classified, the process of FIG. 3 proceeds to stage 58.

At stage 58, the voxel processing circuitry 38 selects a frame for processing, where the frame is selected in dependence on the order of priority determined at stage 42. In a first instance of stage 58, the selected frame is the top priority frame which has priority value 1. Subsequent frames are processed in order of increasing priority value.

At stage 60, the voxel processing circuitry 38 selects a voxel of the selected frame for processing, which in the first instance is a voxel of the top priority frame. The selected voxel is a voxel of the set of voxels classified as material region or a voxel of the set of voxels classified as interior void.

In the embodiment of FIG. 3, an order in which voxels are selected for processing is dependent on the viewing direction. Voxels of the selected frame that are closer to a notional viewer in relation to the viewing direction may be processed before voxels of the frame that are further from the notional viewer. This order of traversing the frame may allow occlusion calculations to be reuse when occlusion is calculated as described below with reference to stage 64. For more complex occlusion metrics, the traversal may be different from a straightforward traversal relative to the viewing direction.

Additional temporary storage may be used. In further embodiments, voxels of the selected frame may be processed in any suitable order.

At stage 62, the voxel processing circuitry 38 determines whether any voxel value has yet been written to a voxel location corresponding to the selected voxel. In the case of the first frame to be processed, which is the top priority frame, no voxel values have yet been written to any voxel locations. The process of FIG. 3 proceeds to stage 64.

At stage 64, the voxel processing circuitry 38 determines an occlusion level associated with the selected voxel. Occlusion levels are described further below with reference to FIG. 5. In the case of the first frame to be processed, there is no occlusion so an occlusion level is 0.

The voxel processing circuitry 38 writes the occlusion level for the voxel to a corresponding voxel location in an object occlusion index 66.

Since there is no occlusion in the case of the top priority frame, the voxel processing circuitry 38 does not divide any objects in accordance with the occlusion. Such division of objects is described below with reference to stage 64 as performed on a subsequent frame.

At stage 68, the voxel processing circuitry 38 performs a delineation procedure. The delineation procedure of stage 68 is optional and may be omitted in some embodiments. The delineation procedure is used to insert an artificial gap between objects when combining objects from different frames.

In the delineation procedure, the voxel processing circuitry 38 identifies whether the selected voxel belongs to a boundary of an object to which it is assigned. If the voxel belongs to the boundary, it is removed from the object in the delineation procedure. By removing boundary voxels, a gap is created between objects when the objects are rendered.

In other embodiments, voxels belonging to the boundary are added to a border region, which is treated as a further object. The border region is used to create a gap between objects when rendering.

By creating an artificial gap between objects, the boundary between objects from different frames may be highlighted in a rendered image. Highlighting the boundary between objects may highlight that the content comes from different frames. Using a delineation procedure to highlight the difference between objects may be particularly useful when there is not a large difference in color between the objects in the rendering.

At stage 70, the voxel processing circuitry 38 writes the voxel value for the voxel to a corresponding voxel location in a volume 72. The voxel processing circuitry 38 also writes the label that was determined at stage 68 to a corresponding voxel location in a segmentation volume 74.

At stage 76, the processing of the voxel is done. If more voxels in the material region and interior void of the selected frame remain to be processed, the method of FIG. 3 returns to stage 60 and another voxel is selected. If all voxels in the material region and interior void of the selected frame have been processed, the method of FIG. 3 returns to stage 58.

At stage 58, the voxel processing circuitry 38 selects a next frame for processing, where the frame is selected in accordance with the order of priority determined at stage 42. The next frame selected has a priority value that is 1 higher than its preceding frame.

At stage 60, the voxel processing circuitry 38 selects a voxel of the selected next frame for processing. The selected voxel is a voxel of the set of voxels classified as material region or a voxel of the set of voxels classified as interior void in the selected next frame. In the embodiment of FIG. 3, an order in which voxels are selected for processing is dependent on the viewing direction as described above, such that voxels that are closer to a notional viewer may be processed before voxels of the frame that are further from the notional viewer.

At stage 62, the voxel processing circuitry 38 determines whether any voxel value has yet been written to a voxel location corresponding to the selected voxel, for example by consulting the volume 72. If a voxel value has already been written to the voxel location, the method of FIG. 3 proceeds to stage 76 and the processing of the voxel is done.

If no voxel value has yet been written to the voxel location, the method of FIG. 3 proceeds to stage 64. In the case of the second frame in the order of priority, voxels that have already been written are voxels that fall within the material region or interior void of the first frame. If a voxel of material region or interior void in the second frame is in a voxel location that has not yet been written, it is because of a difference in position of the material region or interior void in the second frame when compared with the top priority frame. The process of FIG. 3 therefore distinguishes voxels of the second frames that may be indicative of movement relative to the top priority frame.

Similarly, for subsequent frames, the voxel locations where no voxel value has yet been written are voxel locations that did not form part of the material region or interior void in any of the higher-priority frames.

At stage 64, the voxel processing circuitry 38 determines an occlusion level associated with the selected voxel. The occlusion level is zero if the voxel is determined to be non-occluding. The occlusion level is non-zero if the voxel is determined to be occluding. Occlusion levels are described further below with reference to FIG. 5.

Occlusion is determined using an occlusion heuristic. The occlusion heuristic estimates areas in which a lower-priority object occludes a higher-priority object from the viewing direction and separates these areas as a segmentation hierarchy.

In the embodiment of FIG. 3, the occlusion heuristic makes use of a straight line of sight from the viewer. A voxel is determined to be occluding if it lies in a straight line of sight between the viewer and one or more voxels of a higher-priority object. If more than one higher-priority object is present in the line of sight, the voxel may be determined to be occluding if it lies in a straight line of sight between the viewer and a frontmost one of the higher-priority objects. In alternative embodiments, the voxel may be determined to be occluding if it lies in a straight line of sight between the viewer and any one of the higher-priority objects.

In other embodiments, the occlusion heuristic determines a voxel to be occluding if it lies within an angular range determined relative to a voxel of a higher-priority object, for example within a cone that extends from the voxel of the higher-priority object towards the viewer.

If parallel projection is used, a viewing direction of the parallel projection may be used in the occlusion heuristic.

In modalities with a preferred viewing axis or direction, the occlusion heuristic may limit the determination of occlusion to the preferred viewing axis or direction. In some circumstances, ultrasound or magnetic resonance images may have a preferred viewing axis or direction, for example always viewing around a direction of a probe or a direction of a main scan. A voxel may be determined to be occluding if lies between the viewer and a higher-priority object on a preferred viewing axis.

In further embodiments, any suitable method of determining whether the voxel is occluding may be used.

If the voxel is determined to be occluding based on the occlusion heuristic in use, the voxel processing circuitry 38 assigns an occlusion level based on what is being occluded. If the voxel only occludes voxels from one or more higher-priority objects that have an occlusion level of 0 (not occluding), then the voxel processing circuitry 38 assigns an occlusion level of 1. If the voxel occludes any voxel from a higher-priority object than has an occlusion level of 1, then the voxel processing circuitry 38 assigns an occlusion level of 2.

It is noted that occlusion is determined relative to higher-priority objects, which are objects that have been obtained from previous, higher-priority frames.

In some embodiments, an occlusion level determined for one or more preceding voxels may be reused when making a determination for a current voxel. For example, if occlusion is defined along a single axis, voxels may be traversed along that access, reusing what is known from previous voxels when making a determination for a current voxel.

A voxel may be assigned to one of two or more portions of a given object based on the occlusion level of the voxel.

For example, voxels of a material region may be assigned to one portion of the material region if they have been determined at stage 64 to have an occlusion level of 0, and to a different portion of the material region if they have been determined to have an occlusion level of 1. The different portions may be assigned different labels. Voxels that are determined to occlude a first object may be assigned to a different portion, and given a different label, from voxels that are determined to occlude a second, different object, for example an object from a different frame.

At stage 68, the voxel processing circuitry 38 performs a delineation procedure. The delineation procedure of stage 68 is optional and may be omitted in some embodiments. The delineation procedure is used to insert an artificial gap between objects when combining objects from different frames.

In the delineation procedure, the voxel processing circuitry 38 identifies whether the selected voxel belongs to a boundary of an object to which it is assigned. If the voxel belongs to the boundary, it is removed from the object in the delineation procedure. By removing boundary voxels, a gap is created between objects when the objects are rendered.

In other embodiments, voxels belonging to the boundary are added to a border region, which is treated as a further object. The border region is used to create a gap between objects when rendering.

Figure 5:
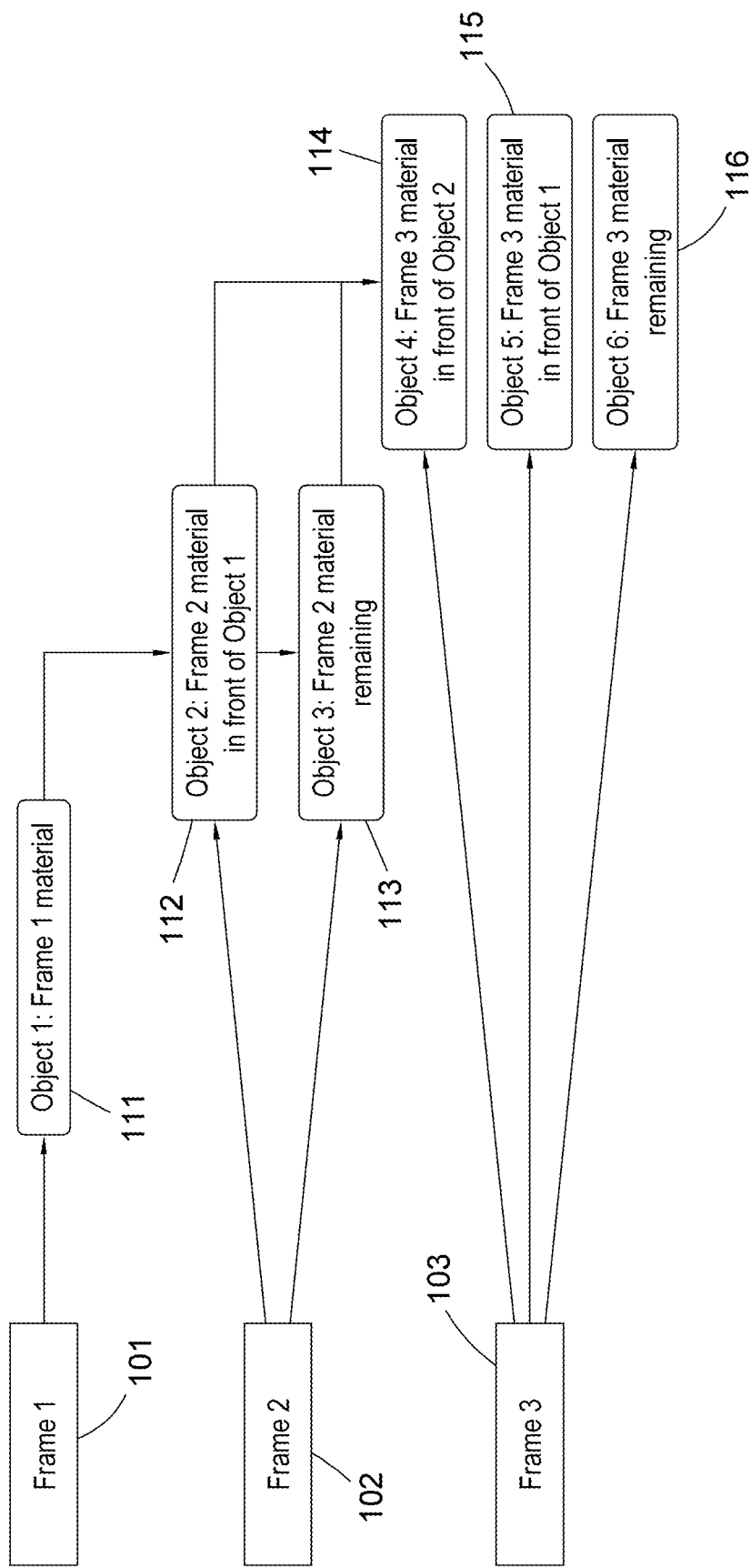
FIG. 5 is a chart illustrating in overview an example of an occlusion tree for objects from three frames.

FIG. 5 is a chart illustrating in overview an example of an occlusion tree for objects from three frames. An object hierarchy may be formed based on the occlusion tree. The object hierarchy may be determined using the occlusion determination of stage 64.

Frame 1, 101, is a top priority frame so is the first frame in the order of priority. Object 1, 111, comprises the material that is present in Frame 1. Voxels of Object 1 are assigned an occlusion level of 0 since they are non-occluding.

Frame 2, 102, is the second frame in the order of priority. The material that is present in Frame 2 is divided into two objects. Object 2, 112, comprises the portion of the material that is present in Frame 2 that is determined to be in front of, and occluding, Object 1. Voxels of Object 2 are assigned an occlusion level of 1 since they occlude Object 1. Object 3, 113, comprises a remaining portion of the material that is present in Frame 2, which is not determined to be in front of Object 1. Voxels of Object 3 are assigned an occlusion level of 0 since they are non-occluding.

Frame 3, 103, is the second frame in the order of priority. The material that is present in Frame 3 is divided into three objects. Object 4, 114, comprises the portion of the material that is present in Frame 3 that is determined to be in front of, and occluding, Object 2. It is noted that Object 2 comprises the material of Frame 2 that was determined to be in front of, and occluding, Object 1. Therefore, Object 4, 114, comprises material that is in front of, and occluding, both Object 1 and Object 2.

Voxels of Object 4 are assigned an occlusion level of 2 since they occlude an object, Object 2, which is itself occluding and has an occlusion level of 1.

Object 5, 115, comprises the portion of the material that is present in Frame 3 that is determined to be in front of, and occluding, Object 1, but is not in front of Object 2.

Voxels of Object 4 are assigned an occlusion level of 1 since they occlude an object, Object 1, which is not an occluding object.

Object 6, 116, comprises the remaining portion of the material that is present in Frame 3, which is not determined to be in front of Object 1 or Object 2. Voxels of Object 6 are assigned an occlusion level of 0 since they are non-occluding.

In general, an occlusion level for voxels of an occluding object may be obtained by adding 1 to the highest occlusion level of any object that is being occluded by the occluding object.

The occlusion tree of FIG. 5 may be used at a subsequent rendering stage, for example the rendering stage 80 as described below. The occlusion tree may be used to obtain an opacity formula to guarantee a pixel contribution when rendering a set of occluding objects. For example, in the case of Object 4 occluding Object 2 which itself occludes Object 1, the opacity formula may specify that Object 1 accounts for 50% of opacity, Object 2 for 25% of opacity, and Object 4 for 25% of opacity.

Turning back to FIG. 3, after stage 68 the method of FIG. 3 proceeds to stage 70. At stage 70, the voxel processing circuitry 38 writes the voxel value for the voxel to a corresponding voxel location in the volume 72. The voxel processing circuitry 38 also writes the label that was determined at stage 66 to a corresponding voxel location in the segmentation volume 74.

At stage 76, the processing of the voxel is done. If more voxels in the material region and interior void of the selected frame remain to be processed, the method of FIG. 3 returns to stage 60 and another voxel is selected. If all voxels in the material region and interior void of the selected frame have been processed, the method of FIG. 3 returns to stage 58.

Stages 58 to 76 are repeated until all voxels of material and interior frames in all frames of the frame set have been processed. The voxel processing algorithm of FIG. 3 is then done at stage 78.

At stage 80, the rendering circuitry 39 renders an image using the volume 72 and segmentation volume 74. Any suitable rendering method may be used. For example, the rendering method may comprise shaded volume rendering. The rendering method may comprise unshaded volume rendering. The rendering method may comprise global illumination.

Objects may be split into occluding and non-occluding portions, for example as described above with reference to FIG. 5. In the rendering of stage 80, occluding portions of objects may be rendered with greater transparency than non-occluding portions. In alternative embodiments, occluding portions of objects may be omitted from the rendering. In further embodiments, any suitable visual effects may be applied to the objects, for example any suitable color, opacity, reflectivity or texture. The visual effects used may differ between an occluding portion of an object and a non-occluding portion of the same object. Different objects may be rendered using different visual effects.

A resulting rendered image may be displayed on a screen, for example on display screen 26. The rendered image may be displayed to a user, for example a clinician.

In the method of FIG. 3, frames are ordered by priority. Segmentation is used to drive merging of data from multiple frames into a single image. Segmented objects from different frames are aligned in a combined image. Segmentation is divided based on occlusion.

Instead of combining whole frames, for example by using image fusion, the algorithm of FIG. 3 combines frames by priority order according to frame sequence. Voxels of multiple frames are combined into a single data set. For each voxel, the algorithm determines which frame supplies the voxel value for that voxel. The use of a single data set may make rendering faster and/or more efficient than, for example, fusion rendering methods in which multiple data sets are rendered at once. In some circumstances, fusion may be considered to be very heavyweight in terms of resource usage.

The method of FIG. 3 relies on segmentation to adjust what space to combine and what space to leave for the next frame. Material is cherry-picked to avoid excessive combination.

Segmentation is used to distinguish which voxels belong to which frame of the frame set. A contribution of the frames is divided into segmentation objects.

Occlusion is addressed by using an occlusion heuristic to separate occluding material into its own segmentation hierarchy. The segmentation includes information about how objects occlude one another.

The method of FIG. 3 provides a processing scheme that may be used to create volume rendered action sequences from mainly temporal data sets. The processing aims to avoid scene clutter by combining frames by priority and by adjusting segmentation to highlight occluding areas.

Figure 6:
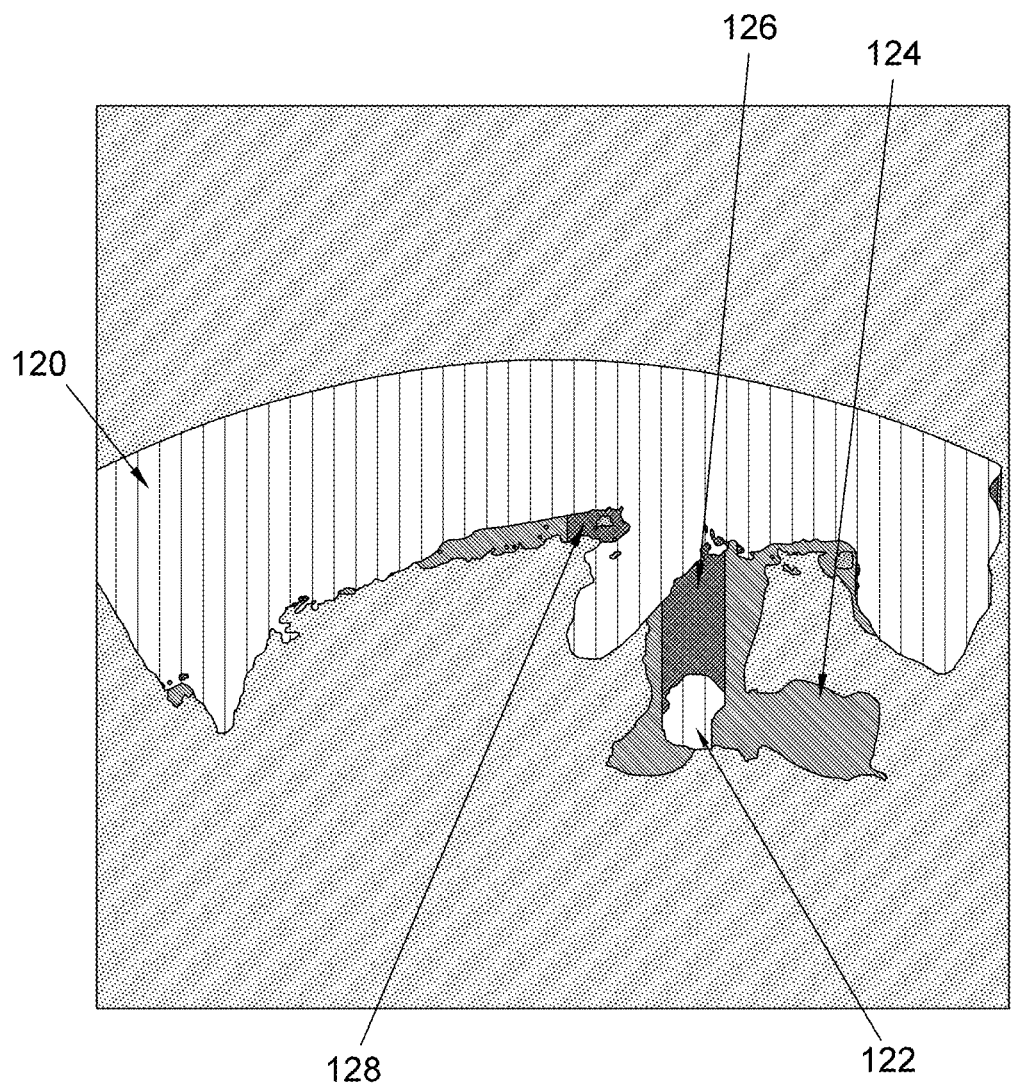
FIG. 6 provides a example of segmentation in an image rendered from an ultrasound volume using a method in accordance with an embodiment.

FIG. 6 provides an example of a segmentation in an image rendered from an ultrasound volume. The ultrasound volume comprises voxels from two frames, Frame 1 and Frame 2. Frame 1 is higher priority than Frame 2.

A y-axis occlusion heuristic is used, in which an occlusion direction on FIG. 6 is downwards. Objects at the bottom of FIG. 6 are in front of objects at the top of FIG. 6.

Regions 120 and 122 are regions of material from Frame 1, which is the higher priority frame. Regions 120 and 122 are shaded using a first shading to represent a first color, for example red.

Region 124 is a region of material from Frame 2 which is in front of a region of material 120 from Frame 1. Region 124 is shaded using a second shading to represent a second color, for example green. When considering the occlusion axis, region 124 lies between the viewer and region 120. Region 124 is considered to be occluding and is given an occlusion level of 1.

Region 126 is another region of material from Frame 2. Region 126 is shaded using a third shading to represent a third color, for example blue. When considering the occlusion axis, region 126 lies between the viewer and region 120. However, region 126 lies behind region 122, which is the frontmost higher-priority region. In the occlusion heuristic of FIG. 6, a region is considered to be occluding if it lies between the viewer and the frontmost higher-priority region. Since region 126 does not lie between the viewer and frontmost region 122 of Frame 1, it is not considered to be occluding and is given an occlusion index of 0.

Region 128 is a further region of material from Frame 2, which lies in front of part of region 120 and behind another part of region 120. Region 128 is shaded with the same shading as region 126. Region 128 is not considered to be occluding because it lies behind the frontmost region in a line of sight from the viewer, which is 120. Region 128 is given an occlusion index of 0.

Region 124 and regions 126 and 128 are treated as separate objects even though they all include material from Frame 2.

FIG. 6 is an example of use of an occlusion heuristic that considers occlusion relative to a frontmost object. In other embodiments, the occlusion heuristic may consider occlusion relative to a backmost object.

If more frames are added to Frame 1 and Frame 2 of FIG. 6, additional objects will be added which may occlude any of the regions shown in FIG. 6. A region of material occluding more than one of the regions shown in FIG. 6 may be split into multiple different objects based on the occlusion properties of each region.

Figure 7A:
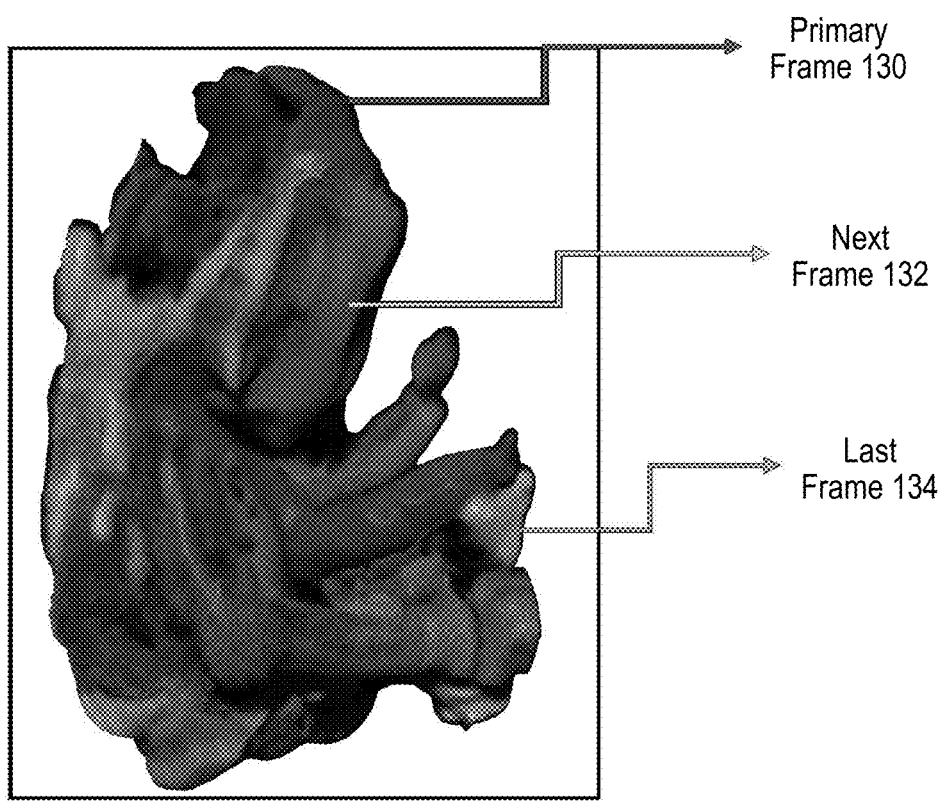
FIG. 7A shows an example of an ultrasound image rendered from three frames using a method in accordance with an embodiment.
Figure 7B:
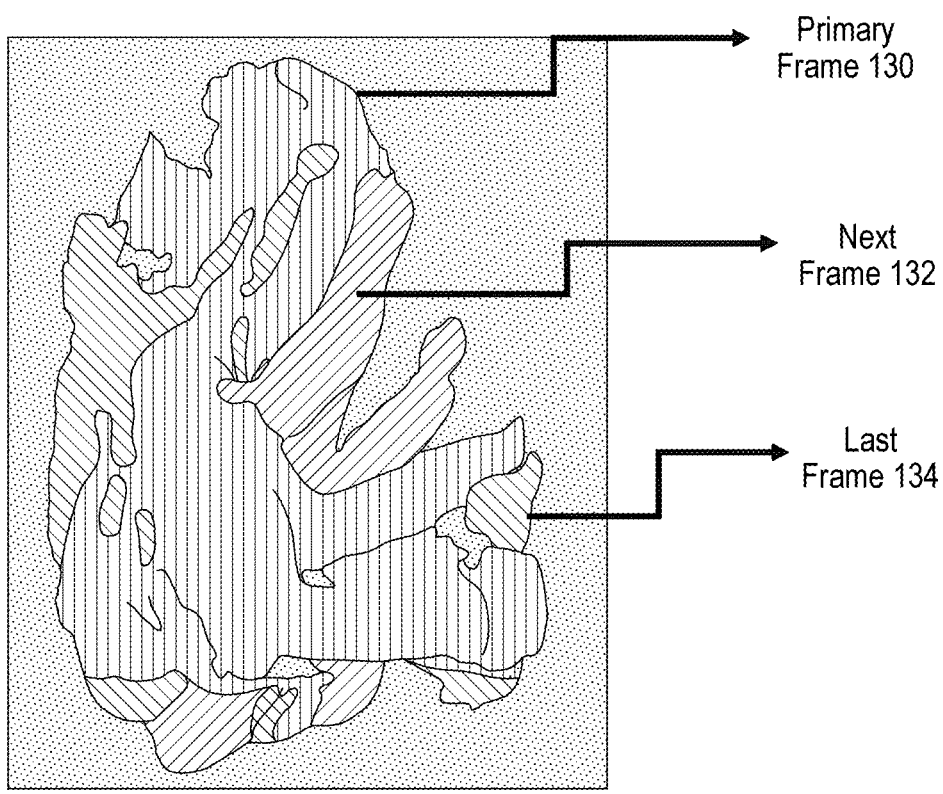
FIG. 7B is a version of the image of FIG. 7A in which different colors are represented by different shading.

FIGS. 7A and 7B show an example of an ultrasound image rendered from three frames using the method of FIG. 3, in which different colors are used to represent different frames. FIG. 7A shows a version of the color image that is reproduced in greyscale. FIG. 7B shows a version of FIG. 7A in which different shading effects are used to represent the different colors that are used to represent the different frames.

Regions of material from the top priority frame 130, which may also be referred to as the primary frame, are rendered in a first color, which is represented by vertical shading in FIG. 7B. Regions of material from the next frame 132, which is second in priority, are rendered in a second color, which is represented by right diagonal shading in FIG. 7B. Regions of material from the last frame 134, which is lowest in priority, are rendered in a third color, which is represented by left diagonal shading in FIG. 7B.

The image of FIGS. 7A and 7B shows movement of a fetus. Movement of the arm may be seen in differently colored renderings of the arm. Some movement of the head is visible.

Figure 8:
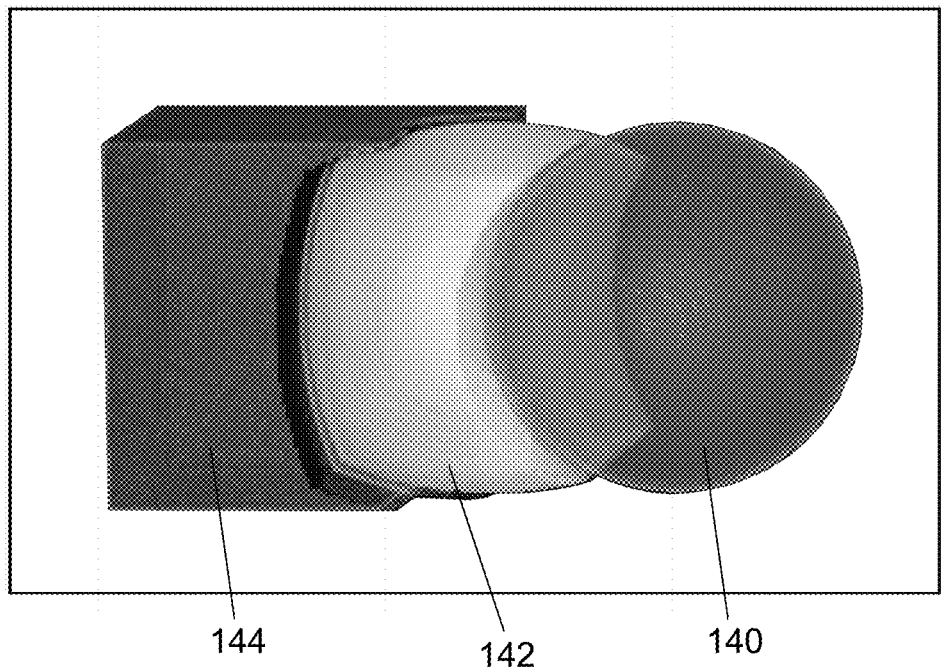
FIG. 8 shows an example of an image rendered using a method in accordance with an embodiment.

FIG. 8 is a rendered image showing a sphere 140 translating left and morphing to a cube 144 via an intermediate shape 142. The method of FIG. 3 is used to summarize movement between three frames (sphere 140, intermediate shape 142, cube 144) into one image or scene. A delineation procedure, for example as described above with reference to stage 68 of FIG. 3, is used to create a gap between objects in the rendered image.

The cube 144 is larger than the sphere 140 and may occlude material. Therefore, a priority order is defined in which the sphere 140 is the highest priority. By setting the sphere 140 as the highest priority object, all of the sphere is kept visible. The intermediate shape 142 is the second priority object and the cube 144 is the lowest priority object.

Opacity may be controlled based on occluding properties. A segmentation as described with reference to FIG. 3 may be used to cut away material that is occluding a higher priority object.

It is noted that a simple combination of the volumes of the sphere 140, intermediate shape 142 and cube 144 would let the cube 144 of the final frame obscure the other frames. The method of FIG. 3 separates the material into new labels that the rendering circuitry 39 can determine how to render.

The translation of the object and its shift from sphere 140 to cube 144 are combined into one scene thanks to the method of FIG. 3.

Figure 9:
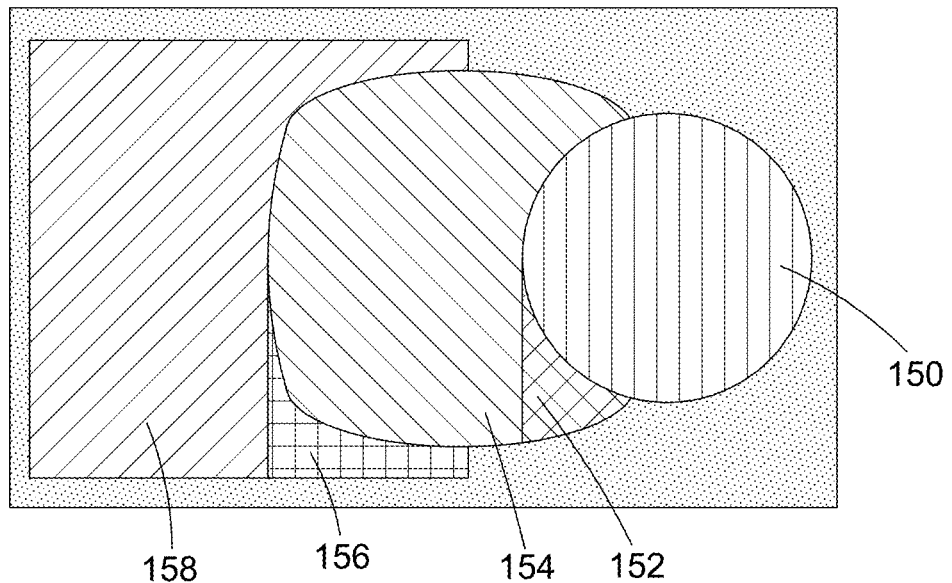
FIG. 9 shows a segmentation corresponding to the image of FIG. 8.

FIG. 9 shows a segmentation of the objects of FIG. 8. In FIG. 8, an object is considered to occlude another object when it is further towards the top of FIG. 8 than the other object. A first segmentation object 150 includes voxels of the sphere 140. Second and third segmentation objects 152, 154 include voxels of the intermediate shape 142. The second segmentation object 152 includes voxels that occlude the first segmentation object 150, and the third segmentation object 154 includes voxels that do not occlude any other segmentation object.

Fourth and fifth segmentation objects 156, 158 include voxels of the cube 144. Fourth segmentation object 156 includes voxels that occlude the third segmentation object 154. Fifth segmentation object 158 includes voxels that do not occlude any other segmentation object.

In the segmentation of FIG. 9, it can be seen that the method of FIG. 3 has generated objects to deal with occluding material.

In rendering, the occluding material of third and fifth segmentation objects 154, 158 may be rendered with low opacity or may be omitted entirely. In other embodiments, the occluding material may be rendered using a different color or other image property when compared with non-occluding material of the same frame.

FIGS. 10A to 10F show a combination of frames in which multiple objects are present.

Figure 10A:
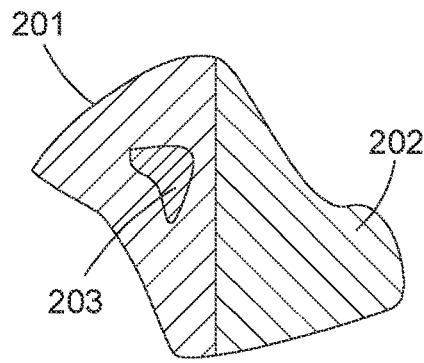
FIG. 10A represents a first frame including two objects.
Figure 10B:
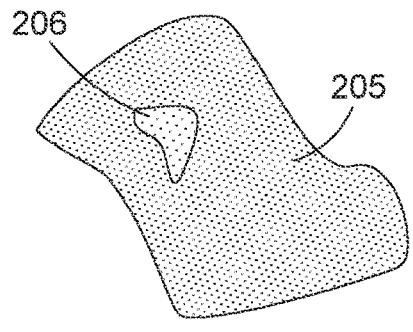
FIG. 10B represents a material region of the first frame.

FIG. 10A represents a first frame including two objects 201 and 202. Object 201 contains a void 203. FIG. 10B represents a material region 205 of the first frame, which is a union of the material of objects 201 and 202. FIG. 10b also shows a region of interior void 206 comprising the void 203 in object 201, and a region of exterior void 207, which is space that is not occupied by the objects 201 and 202.

Figure 10C:
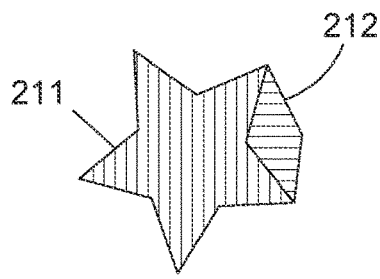
FIG. 10C represent a second frame including two further objects.
Figure 10D:
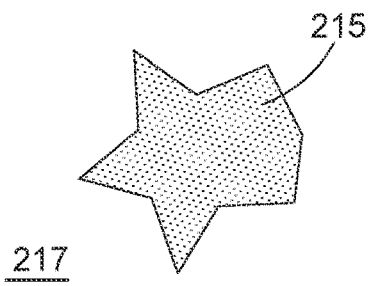
FIG. 10D represents a material region of the second frame.

FIG. 10C represents a second frame including two further objects 211 and 212. FIG. 10D represents a material region 215 of the second frame, which is a union of the material of objects 211 and 212. FIG. 10D also shows an exterior void 217, which is space that is not occupied by the further objects 211 and 212.

Figure 10E:
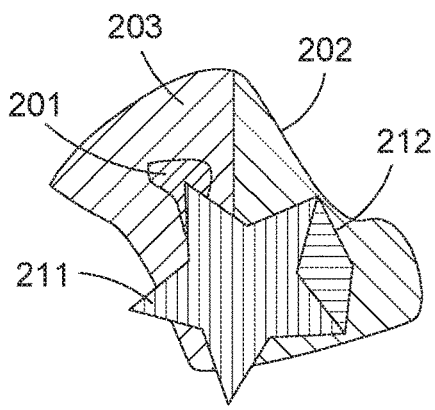
FIG. 10E represents the objects of the first and second frames before occlusion is determined.

FIG. 10E represents the objects 201, 202 and void 203 of the first frame and further objects 211, 212 of the second frame before occlusion is determined. The further objects 211, 212 of the second frame are prioritized over the objects 201, 202 of the second frame.

Figure 10F:
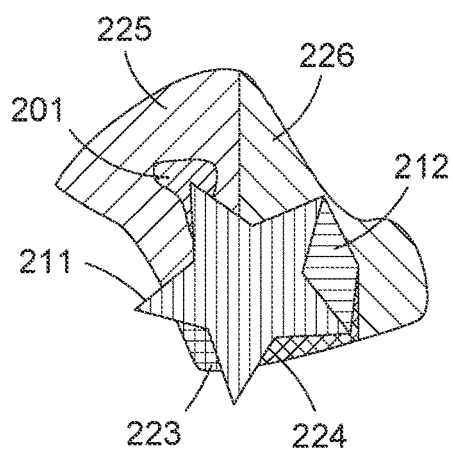
FIG. 10F represents the objects of the first and second frames after occlusion is determined.

FIG. 10F represents the objects of the first and second frames after occlusion is determined. The process of determining occlusion divides the first object 201 into an occluding object 223 and a non-occluding object 225. The process of determining occlusion divides the second object 202 into an occluding object 224 and a non-occluding object 226.

When occlusion is determined, the material region 215 of the second frame is considered as a whole. The occluding objects may occlude either or both of the first and second further objects 211, 212. For example, a first part of occluding object 224 occludes further object 211, and a second part of occluding object 224 occludes further object 212.

However, the occluding objects 223 and 225 and non-occluding objects 224 and 226 are each formed from a single one of the original objects 201, 202. For example, a first occluding object 223 is formed from object 201 and a second, different occluding object 225 is formed from object 202.

It is not necessary for a number of objects in a first frame to be the same as a number of objects in a second or subsequent frame. Any number of objects may be present in each of the frames.

In further embodiments, data from each frame may be offset such that the objects from different frames appear more separated. For example, if there is lateral movement between frames, objects from the frames may also be offset in an upwards direction to create additional separated. Adding an offset may make the objects appear more separated and so make movement easier to distinguish. Data for each frame may be offset to create better separation for specific anatomy, creating a slightly larger volume.

In embodiments described above, a single priority ordering of frames is used, with a single frame being the top priority frame. In other embodiments, a priority ordering may be cycled such that different frames become the top priority frame in turn. For example, frames may be cycled from future to current and then to the past. By cycling frames in the priority, an animation may be created in which the highlighted material changes with the frame, but a sum of the content is preserved.

In embodiments described above, the frame set comprises image data obtained in a succession of image acquisitions, for example as frames of a four-dimensional image acquisition. In other embodiments, any suitable frame set may be used. For example, the frame set may comprise frames obtained from different acquisitions performed at different times, for example frames obtained by imaging the same patient on different days, different weeks, different months or different years. The frame set may comprise frames obtained by imaging different patients or other subjects. The frame set may comprise image data obtained by gated image acquisition, for example images of gated cardiac phases or dynamic scan angiography phases.

The method of FIG. 3 may be used to measure either short term differences (for example, movement between frames of a four-dimensional data set) or long term differences (for example, disease progression between different scans).

In further embodiments, the method of FIG. 3 may be used to combine any suitable images. For example, the method of FIG. 3 may be used to show registration error by comparing a first image and a second image, where an attempt has been made to register the second image to the first image. The first image may be referred to as a target image. If the registration is successful, it may be the case that there is little to no difference in the images and the resulting combined image may look similar to the first image. If the registration is less successful, a difference between the images may be highlighted in the combined image.

In some embodiments, a volume may be reprocessed if the user rotates the view by a sufficient amount. For example, the reprocessing may comprise repeating stages 58 to 76 of the method of FIG. 3 for a new viewing direction.

In the method of FIG. 3, occlusion is based on viewing direction. If the viewing direction is changed, voxels that had previously been occluding may become non-occluding and/or voxels that had previously been non-occluding may become occluding. A reprocessing may result in an updated segmentation volume 74.

The rendering circuitry 39 may use the updated segmentation volume in rendering an updated combined image. The updated combined image is viewed from a different viewing direction and may also differ from an original combined image in which regions are occluding.

In some embodiments, a threshold may be applied to a change in viewing direction such that reprocessing only occurs for a change in viewing direction that is large enough to exceed the threshold. If the change in viewing direction is smaller than the threshold, the rendering circuitry 39 may reuse the existing volume 72 and segmentation volume 74.

In other embodiments, the modality of the medical image data exhibits a principal viewing direction and no change in viewing direction is made. In such embodiments, the method of FIG. 3 is performed only once.

Embodiments described above comprises determining combining data from a plurality of frames each comprising medical image data, for example ultrasound data. In other embodiments, any suitable medical image data may be used, which may be of any suitable modality or modalities. The medical image data may be representative of any human or animal subject.

In further embodiments, the frames may each comprise any suitable type of data, which may not be medical image data.

Certain embodiments provide a medical image display apparatus comprising processing circuitry configured to:
receive plurality of time phase medical image data, specify parameters relating to priority in each medical image data within the plurality of time phase medical image data, select more than one of the medical image data within the plurality of time phase medical image data based on the parameters, generate combined image data by combining the selected medical image data.

The combined image data may be generated by combining the selected medical image data, wherein the selected medical image data is aligned based on the parameters.

Certain embodiments provide a medical imaging method comprising:
A temporal sequence of frames
A frame priority order
A set of segmentation objects per frame indicating relevant/irrelevant tissue
In which data described by the segmentation from each frame is combined, separating the contribution in the joint volume segmentation.

An occlusion heuristic may estimate the areas where a lower priority object occludes a higher priority object from the viewing direction and separate these areas as a segmentation hierarchy.

The frame priority may be current frame and only past frames in order from the current frame.

The frame priority may be current frame and only future frames in order from the current frame.

The frame priority may be current frame and past frames as well as the last future frame.

The frame priority may be current frame and alternating past/future frames to keep temporal distance.

The occlusion heuristic may be straight line of sight from the viewing direction.

The occlusion heuristic may be an angular range centered on the line of sight.

The volume may be reprocessed as the user rotates the view sufficiently.

The modality may exhibit a principal viewing direction and the processing may only happen once.

A staggered frame offset may be created to separate features more across frames, even when they don't move laterally.

Gated cardiac phases may be shown. Dynamic scan angiography phases may be shown.

Registration error may be shown using the same processing.

A view may be animated by multiple processing in which frames are cycled from future to current and then to the past.

Certain embodiments provide a medical image processing apparatus comprising processing circuitry configured to: receive a plurality of sets of frame data, each set of frame data representative of a scene at a respective different time; obtain a segmentation of at least one tissue or other feature of interest in at least some of the frames; and combine data from the plurality of sets of frame data to produce a single image representing the scene at a plurality of different times, wherein the combining of the data comprises spatially separating in the image, at least partially, representations of the tissue(s) or other feature(s) of interest at the different times, and using the segmentations to exclude at least some data from the combined image.

The combining of the data to produce the single image may comprise assigning priorities to different ones of the segmentations, and using the assigned priorities to reduce or eliminate occlusion.

The processing circuitry may be configured to establish a frame priority order, and the obtaining of a segmentation may comprise obtaining a set of segmentation objects per frame representing relevant or irrelevant tissue.

An occlusion heuristic may be used to estimate the areas where a lower priority object occludes a higher priority object from a viewing direction and separates these areas as a segmentation hierarchy.

The frame priority may comprise at least one of:
a) current frame and only past frames in order from the current frame;
b) current frame and only future frames in order from the current frame;
c) current frame and past frames as well as the last future frame;
d) current frame and alternating past/future frames to keep temporal distance.

The occlusion heuristic may comprise a straight line of sight from the viewing direction; or the occlusion heuristic may comprise an angular range centered on the line of sight.

The processing circuitry may be configured to at least one of:
a) repeat the segmenting and/or combining in response to a user rotating a view;
b) in response to there being a principal viewing direction perform the segmenting and/or combining only once;
c) create a staggered frame offset to separate features more across frames, even when they don't move laterally;

d) show gated cardiac phases or dynamic scan angiography phases;
e) show registration error;
f) animate a view by cycling frames from future to current and then to the past.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image display apparatus, comprising:
processing circuitry configured to:
receive a plurality of frames acquired at different times or time phases, each comprising respective medical image data;
specify an order of priority for the plurality of frames;
select one or more frames from the plurality of frames based on the order of priority;
classify at least one segmentation object of segmentation objects included in the one or more selected frames; and
generate combined image data by combining the one or more selected frames, such that the at least one segmentation object of the segmentation objects of the one or more selected frames are aligned with each other in the combined image data.

2. The apparatus according to claim 1, wherein the processing circuitry is further configured to render an image from the generated combined image data.

3. The apparatus according to claim 2, wherein the processing circuitry is further configured to apply an offset to regions from different ones of the plurality of frames, thereby to visually separate regions from different ones of the plurality of frames in the rendered image.

4. The apparatus according to claim 2, wherein the processing circuitry is further configured to render further images using different orders of priority for the plurality of frames, thereby to cycle between current frames to create an animated view.

5. The apparatus according to claim 1, wherein in performing the combining, the processing circuitry is further configured to estimate an occluding region in which a first segmentation object from a first frame of the plurality of frames occludes a second segmentation object of a second, different frame of the plurality of frames when viewed from a viewing direction.

6. The apparatus according to claim 5, wherein the first frame is lower in the order of priority than the second frame.

7. The apparatus according to claim 5, wherein in performing the estimating, the processing circuitry is further configured to estimate the occluding region based on at least one of a straight line of sight from the viewing direction, and an angular range around a line of sight from the viewing direction.

8. The apparatus according to claim 5, wherein the processing circuitry is further configured to adjust at least one rendering parameter of the occluding region based on the estimated occlusion.

9. The apparatus according to claim 5, wherein the processing circuitry is further configured to perform a reprocessing procedure in response to a change in viewing direction, the reprocessing procedure comprising updating the estimating of the occluding region based on the updated viewing direction.

10. The apparatus according to claim 5, wherein the viewing direction is a principal viewing direction of an imaging modality in which the plurality of frames are acquired.

11. The apparatus according to claim 1, wherein the processing circuitry is further configured to assign a respective occlusion index value to each segmentation object, wherein the occlusion index value is dependent on whether the segmentation object is occluding of one or more further segmentation objects.

12. The apparatus according to claim 1, in which the specifying of the order of priority by the processing circuitry comprises at least one of:
selecting a current frame and a set of past frames in order from the current frame;
selecting the current frame and a set of future frames in order from the current frame;
setting the current frame, the set of past frames in order from the current frames, and a last future frame; or
selecting the current frame and the set of past and future frames in alternating order so as to keep an order of temporal distance from the current frame.

13. The apparatus according to claim 1, wherein the segmentation objects comprise two or more of a material, an interior void, an exterior void, and a signal void.

14. The apparatus according to claim 1, wherein the processing circuitry is further configured to perform a rigid or non-rigid registration to align the segmentation objects before the combining.

15. The apparatus according to claim 1, wherein the plurality of frames are representations of gated cardiac phases or dynamic scan angiography phases.

16. The apparatus according to claim 1, wherein a first frame of the plurality of frames is representative of a target image for a registration, a second frame of the plurality of frames is representative of an image to which the registration has been applied, and the combined image data is representative of a registration error.

17. A method, comprising:
receiving a plurality of frames acquired at different times or time phases, each comprising respective medical image data;
specifying an order of priority for the plurality of frames;
selecting one or more frames from the plurality of frames based on the order of priority;
classifying at least one segmentation object of segmentation objects included in the one or more selected frames; and
generating combined image data by combining the one or more selected frames, such that the at least one segmentation object of the segmentation objects of the one or more selected frames are aligned with each other in the combined image data.

* * * * *